United States Patent [19]
Verdicchio et al.

[11] Patent Number: 4,948,576
[45] Date of Patent: Aug. 14, 1990

[54] DETERGENT COMPOSITIONS

[75] Inventors: Robert J. Verdicchio, Succasunna; Diane L. Spilatro, Piscataway, both of N.J.

[73] Assignee: Johnson & Johnson Consumer Products, Inc., New Brunswick, N.J.

[21] Appl. No.: 468,120

[22] Filed: Feb. 18, 1983

[51] Int. Cl.⁵ .......................... A61K 7/06; A61K 7/08; A61K 31/215
[52] U.S. Cl. ................................ 424/59; 252/174.16; 424/DIG. 4; 424/70; 514/65; 514/864; 514/880; 514/888; 514/919
[58] Field of Search ........................... 424/59, DIG. 4; 252/174.16

[56] References Cited

U.S. PATENT DOCUMENTS

| | | | |
|---|---|---|---|
| 2,781,382 | 2/1957 | Mannheimer | 260/401 |
| 2,970,160 | 1/1961 | Walker | 260/404.5 |
| 3,954,846 | 5/1976 | Grignard | 260/501.15 |
| 4,181,634 | 1/1980 | Kennedy et al. | 252/545 |
| 4,185,106 | 1/1980 | Dittmar et al. | |
| 4,265,782 | 5/1981 | Armstrong et al. | 252/174.16 |
| 4,369,134 | 1/1983 | Deguchi et al. | 252/174.16 |
| 4,372,869 | 2/1983 | Lindemann et al. | 252/174.16 |

Primary Examiner—Dale R. Ore
Attorney, Agent, or Firm—Steven P. Berman

[57] ABSTRACT

This invention relates to detergent compositions comprising at least one surfactant, at least one water-soluble nitrogen-containing polymer and a water-soluble, non-particulate substance capable of imparting a desired residual effect to a specific substrate such as the scalp or skin.

13 Claims, No Drawings

DETERGENT COMPOSITIONS

BACKGROUND OF THE INVENTION

The present invention relates to detergent compositions. More particularly, this invention relates to shampoo and/or other detergent compositions containing specific antimicrobial agents including antidandruff agents and/or sunscreen agents having improved activity. This invention also relates to composition containing insecticide agents.

Various substances having antimicrobial and antidandruff properties as well as substances having sunscreening properties are well-known in the art and have been incorporated in detergent compositions in general and in particular in shampoo compositions. The activity of these substances in detergent compositions appears to be due in part to the fact that they are deposited on the hair and scalp surfaces or skin surfaces and are retained thereon through the rinsing step. It has generally been found, however, that only a relatively small proportion of such substances present in the detergent compositions actually deposit on the washed surface and survive the rinsing operation.

Since sustained activity of these substances is in part a function of the quantity of the substance deposited and retained, measures which enhance deposition or promote retention will permit either reduction of the quantity of the substance required to attain a given level of activity or will increase the activity attainable using a given concentration of such substance.

U.S. Pat. No. 3,580,853 discloses detergent compositions containing water-insoluble, particulate substances, such as antimicrobial agents, and certain cationic polymers which serve to enhance the deposition and retention of the particulate, water-insoluble substances on surfaces washed with the detergent composition. The substances disclosed in this patent include antimicrobial agents and sunscreens; are all particulate in nature having a particle size of from about 0.2 to about 50 microns and are all water-insoluble or sparingly soluble substances. When these substances are utilized in shampoo formulations, the resulting product would be opaque in appearance due to their particulate nature. In many instances such an opaque product is not as aesthetically appealing to the consumer as a clear product. Further, the presence of these substances in particulate form often necessitates the addition of stabilizers to the formulation and these are usually clays which add "dirt" to the formulation thereby decreasing its cleansing ability. Another problem with the use of water-insoluble particulate substances in shampoo formulations is the potential of said substances to lodge in the eye thereby causing irritation and possible damage to the eye. The use of soluble, non-particulate substances as antimicrobial agents, sunscreen agents or insecticide agents is not comtemplated in this prior art teaching.

SUMMARY OF THE INVENTION

It is an object of this invention to provide improved detergent compositions.

It is a further object of this invention to provide detergent compositions with improved antimicrobial and anti-dandruff properties.

It is a still further object of this invention to provide detergent compositions with improved sunscreen properties.

It is another object of this invention to provide improved insecticide compositions.

These and other objects of this invention will be set forth in or be apparent from the following detailed description of the invention.

The foregoing objects and other features and advantages of the present invention are achieved by detergent compositions comprising at least one surfactant, at least one water-soluble nitrogen-containing polymer and a water-soluble, non-particulate substance capable of imparting a desired residual effect to a specific substrate such as the scalp or skin. The balance of the compositions can comprise various cleansing adjuncts, fillers, carriers and the like which are well-known in the art.

DETAILED DESCRIPTION OF THE INVENTION

The surfactants which are useful in the detergent compositions of the present invention include specific anionic and amphoteric surfactants. Specific non-ionic and cationic surfactants may also be used in conjunction with the anionic and amphoteric surfactants.

The anionic surfactants which are useful in the compositions of the present invention include (a) alkyl sulfates of the formula $$R-OSO_3X$$

(b) alkyl ether sulfates of the formula $$R-O-(CH_2-OCH_2)_n-OSO_3X$$

(c) α-olefin sulfonates of the formula $$R-CH_2-SO_3X$$

(d) alkyl sulfosuccinates of the formula

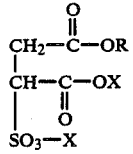

(e) alkyl sarcosinates of the formula

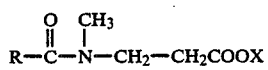

(f) alkyl monoglyceride sulfates of the formula $$R-O-CH_2CH-CH_2-OSO_3X$$
$$\phantom{R-O-CH_2C}|$$
$$\phantom{R-O-CH_2CH-CH}OH$$

(g) alkyl monoglyceride sulfonates of the formula $$R-O-CH_2CH-CH_2-SO_3X$$
$$\phantom{R-O-CH_2C}|$$
$$\phantom{R-O-CH_2CH-CH}OH$$

(h) alkyl benzene sulfonates of the formula

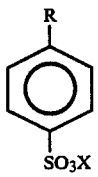

(i) acyl isethionates of the formula

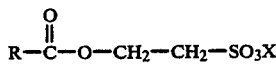

(j) acyl methyl taurides of the formula

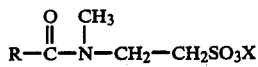

wherein in all of the above R is alkyl of from 8 to 18 carbon atoms and mixtures thereof, X is a water-soluble cation such as sodium, potassium, hydrogen and the like, and n is an integer of from 1 to 5.

The anionic surfactants are useful in the compositions of the present invention in an amount of from about 2 to 20% by weight of the total composition, preferably from about 3 to 7%.

The amphoteric surfactants which are useful in the compositions of the present invention include betaines, sultaines, phosphobetaines, phosphitaines, n-alkylamino propionates, n-alkylimino dipropionates and imidazolines.

The betaine and sultaine surfactants useful in this invention are described in U.S. Pat. No. 3,950,417, which is incorporated herein by reference. The phosphobetaines and phosphitaines useful in this invention are described in U.S. Pat. Nos. 4,215,064 and 4,261,911 which are incorporated herein by reference. The n-alkylamino propionates and n-alkylimino dipropionates are sold under the tradename Deriphats by General Mills. The imidazolines which are useful in the compositions of this invention are described in U.S. Pat. No. 2,970,160 which is incorporated herein by reference.

The preferred betaine amphoteric surfactants include the alkylbetaines such as cocodimethylcarboxymethylbetaine, lauryldimethylcarboxymethylbetaine, lauryldimethylcarboxyethylbetaine, cetyldimethylcarboxymethylbetaine lauryl-bis-(2-hydroxyethyl) carboxymethylbetaine, oleyldimethylgamma-carboxypropylbetaine, lauryl-bis-(2-hydroxypropy)-carboxyethylbetaine, and the like; the sultaines such as cocodimethylpropylsultaine, stearyldimethylpropylsultaine, lauryl-bis-(2-hydroxyethyl) propylsultaine and the like; and the aminosultaines such as cocoamidodimethylpropylsultaine, stearylamidodimethylpropylsultaine, laurylamidobis-(2-hydroxyethyl) propylsultaine, and the like.

The preferred phosphobetaines include lauric myristic amido 3-hydroxypropyl phosphobetaine, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine and the like. The preferred phosphitaines include cocoamido propyl monosodium phosphitaine, lauric myristic amido propyl monosodium phosphitaine and the like.

The preferred n-alkylamino propionates and n-alkylimino dipropionates include those of the following structures:

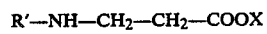

and

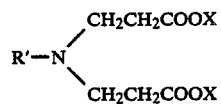

wherein R' is from about 8 to 22 carbon atoms and mixtures thereof and X is as previously defined.

The amphoteric surfactants are useful in the compositions of the present invention in an amount of from about 2 to 20% by weight of the total composition, preferably from about 3 to 5%. If mixtures of anionic and amphoteric surfactants are utilized the total amount of such surfactant mixtures utilized should not exceed about 20% by weight of the total composition.

If desired, nonionic surfactants such as the reaction product of a sorbitan monolaurate or a sorbitan monococoate with 20 to 80 moles of ethylene oxide and the ethoxylated fatty alcohols of the following formula

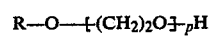

wherein R is as previously defined and mixtures thereof and p is an integer of from 10 to 50; or cationic surfactants such as phosphotriesters of the formula

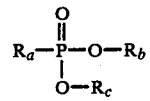

wherein Ra, Rb, and Rc are the same and are selected from the groups consisting of

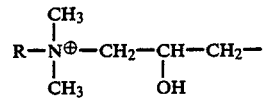

and

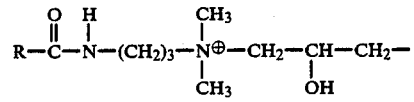

wherein R is as previously defined.

The nonionic surfactants, if utilized, can be present in an amout of from about 0 to 20% by weight of the total composition and the cationic surfactants, if utilized, can be present in an amount of from about 0 to 5% by weight of the total composition.

As hereinbefore indicated, the compositions of this invention contain as an essential component a water-soluble nitrogen containing polymer. Among the water-soluble nitrogen containing polymers that have been found useful are the cationic water-soluble quaternary nitrogen-substituted cellulose ether derivatives and the anionic water-soluble nitrogen containing free sulfonic acid polymers.

The cationic water-soluble quaternary nitrogen-substituted cellulose ether derivatives which are useful are those such as the polymer formed by reacting a hydroxyethylcellulose (having a degree of substitution with hydroxyethyl groups of 1.3) with the reaction product of 0.7 mole of epichlorohydrin and 0.7 mole of trimethylamine, per substituted anhydroglucose unit thereof, said polymer having a cationic charge density of 0.002 and a molecular weight within the range from about 200,000 to 230,000. This polymer has the structural formula:

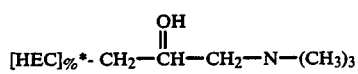

*Hydroxyethylcellulose

Hydroxyethylcellulose is, of course, comprised of hydroxyethyl-substituted anhydroglucose units with varying degrees of hydroxyethyl substitution. This material is prepared by reacting alkaline cellulose with ethylene oxide as is more fully described by Gloor et al., Ind. Eng. Chem., 42:2150 (1950). The extent of substitution with the quaternary nitrogen-containing group must be sufficient to provide a cationic charge density greater than 0.001, and the molecular weight of the substituted hydroxyethylcellulose polymer must be within the range from about 2,000 to 3,000,000.

The preferred cellulose ether derivatives from which the quaternary ammonium-substituted polymers described above are prepared include those which are water-soluble nonionic lower alkyl or hydroxyalkyl substituted. Such derivatives include methylcellulose, ethylcellulose, and hydroxyethylcellulose. A particularly efficacious quaternary ammonium substituted cellulose ether derivative for the purpose of this invention is available from Union Carbide under the tradename Polymer JR. This polymer has a molecular weight within the range from 100,000 to 1,000,000 and a cationic charge density of 0.005. These polymers are disclosed in U.S. Pat. No. 3,580,853, discussed above.

The anionic water-soluble nitrogen containing free sulfonic acid polymers which are useful are polyacrylamidomethylpropane sulfonic acids of the following formula

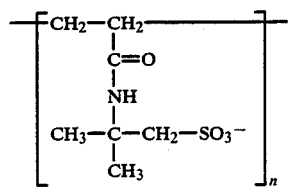

A particularly useful compound is available from Henkel under the tradename Cosmedia Polymer HSP-1180. This compound is a viscous clear liquid with a viscosity of 200,000 cps. and is prepared as a 15% active in water. This compound has an average molecular weight of about 500,000.

The water-soluble nitrogen-containing polymers can be employed herein at a concentration within the range of from about 0.05 to 1.00% by weight of the total concentration, preferably from about 0.1 to 0.3%

Other cationic water-soluble, nitrogen-containing polymers useful in the present invention include:

(a) an adipic acid/dimethylaminohydroxypropyl diethylenetriamine copolymer of the structure

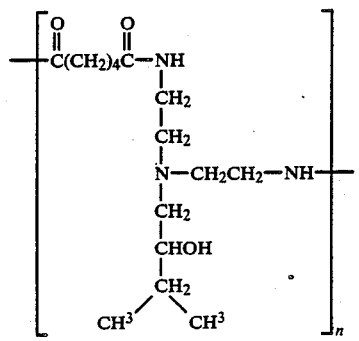

These polymers are available from Sandoz under the tradename Cartaretin and have an average molecular weight of about 10,000.

(b) an acrylamide copolymer of the structure:

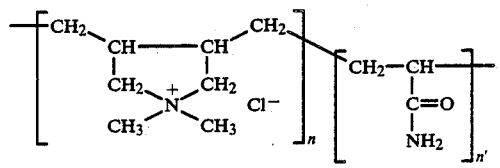

These polymers are available from Merck & Co. under the tradename Merquat and have an average molecular weight of 500,000.

(c) quaternary ammonium polymers formed by the reaction product of dimethyl sulfate and a copolymer of vinyl pyrolidone and dimethylaminoethylmethacrylate. These polymers are available from GAF under the tradename GAFQUAT.

Water-soluble, non-particulate substances which can be utilized in the detergent compositions of this invention include water-soluble antidandruff agents, sunscreens, insecticides and conditioning and emolliency agents. All of these substances depend on deposition and retention on the hair, scalp and/or skin to produce their desired effects.

Water-soluble, non-particulate antidandruff substances whose deposition and retention is enhanced by the water-soluble, nitrogen containing polymers described herein include (a) 1-hydroxy-2-pyridones of the formula

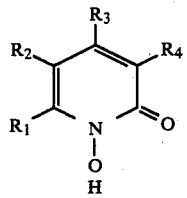

wherein $R_1$ is hydrogen, alkyl of 1 to 17 carbon atoms alkenyl of 2 to 17 carbon atoms, cycloalkyl of 5 to 8 carbon atoms, bicycloalkyl of 7 to 9 carbon atoms, cycloalkyl-alkyl of 1 to 4 alkyl carbon atoms, the cycloalkyl groups being optionally substituted by alkyl groups of 1 to 4 carbon atoms, aryl, aralkyl of 1 to 4 alkyl carbon atoms, aryl-alkenyl of 2 to 4 alkenyl carbon atoms, aryloxy-alkyl or arylthio-alkyl of 1 to 4 alkyl carbon atoms, benzhydryl, phenylsulfonyl-alkyl of 1 to 4 alkyl carbon atoms, furyl or furyl-alkenyl of 2 to 4 alkenyl carbon atoms, the aryl groups being optionally substituted by alkyl of 1 to 4 carbon atoms, by alkoxy of 1 to 4 carbon atoms, by nitro, cyano or halogen atoms. $R_2$ is hydrogen, alkyl of 1 to 4 carbon atoms, alkenyl or alkinyl of 2 to 4 carbon atoms, halogen atoms or benzyl, $R_3$ hydrogen, alkyl of 1 to 4 carbon atoms or phenyl, and $R_4$ is hydrogen, alkyl of 1 to 4 carbon atoms, alkenyl of 2 to 4 carbon atoms, methoxy-methyl, halogen or benzyl, and/or salts thereof.

These compounds are disclosed and more fully described in U.S. Pat. No. 4,185,106 and such compounds are available commercially from Hoechst Aktiengesellschaft under the tradename Octopirox.

(b) magnesium sulfate adducts of 2,2'-dithio-bis(pyridine-1-oxide) of the formula

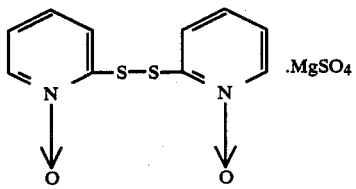

These compounds are available from Olin Corporation under the tradename Omadine MDS.

Other water-soluble non-particulate substances which can be utilized in the present invention include sunscreen agents such as para-amino benzoic acid; and insecticides such as pyrethrin, piperonyl butoxide and mixtures thereof.

The water-soluble, non-particulate substances can be utilized herein within the range of from about 0.1 to 5.0% by weight of the total composition, preferably from about 0.1 to 2.0%.

In addition to the above ingredients, other ingredients conventionally added to detergent compositions for personal use such as dyes, preservatives, perfumes, thickeners, opacifiers, conditioners, emollients, buffering agents and the like, may be added in minor amounts. Ingredients such as dyes, preservatives and perfumes together usually constitute less than 2% by weight of the total composition. The pH of the compositions of this invention are preferably in the range of about 6 to 8.

While applicants do not wish to be bound by the following explanation, it is believed that the unexpected enhanced deposition and retention of the water-soluble non-particulate substances by the water-soluble nitrogen-containing polymers is as a result of coacervation and the formulation of a complex coacervate. This coacervate consists of a basically neutral macromolecule formed by the water-soluble nitrogen-containing polymer/surfactant interaction as a result of changes in the electrokinetic effects brought about primarily by a lowering of the zeta potential of the system as a function of dilution and/or changes in pH. Said polymers and surfactant should be of different electrical charge prior to dilution and subsequent coacervate formation.

Specific embodiments of the detergent compositions prepared in accordance with the present invention are illustrated by the following representative examples. It will be understood, however, that the invention is not confined to the specific limitations set forth in the individual examples, but rather to the scope of the appended claims.

EXAMPLE I

A low-irritating shampoo composition is prepared as follows.

Four grams of Polymer JR are dissolved in 400 grams of deionized water and heated until clear. The following are then added in order, 113.6 grams of a 44% active cocoamido sultaine, 156.3 grams of a 32% active tridecyl alcohol (4.2) ether sodium sulfate, and 166.7 grams of a 72% active polyoxyethylene sorbitan monolaurate followed by 13.0 grams of polyethylene glycol (150) distearate and the mixture is heated until homogeneous. After cooling to 35° C, 10 grams of Omadine MDS are added and mixed until in solution. The pH is adjusted to 6.0 to 6.2 with dilute HCL. 1.0 gram of Dowicil 200 is then added with 3.0 grams of fragrance. Sufficient deionized water is added to bring the total batch weight to 1000 grams. The resulting formulation is a clear dandricidal shampoo of the following composition:

|  | wt/wt% (active) |
| --- | --- |
| cocoamido hydroxypropyl sultaine | 5.00 |
| sodium salt of tridecylether (4.2) sulfate [TDES(4.2)] | 5.00 |
| polyoxyethylene (44) sorbitan monolaurate | 12.00 |
| Omadine MDS | 1.00 |
| polyoxyethylene glycol (150) distearate | 1.30 |
| Polymer JR | 0.40 |
| Dowicil 200 (Dow Chemical's tradename for the cis-isomer of 1-(3-chloroalkyl)-3,5,7-triaza-azoniaadamantine chloride) | 0.10 |
| fragrance | 0.30 |
| deionized water q.s. to | 100.00 |

EXAMPLE 2

A dandricidal detergent composition is prepared according to the process of example 1 and consists of the following ingredients:

|  | wt/wt% |
| --- | --- |
| cocoamidohydroxypropyl sultaine | 5.00 |
| TDES (4.2) | 5.00 |
| polyoxyethylene (44) sorbitan moaurate | 12.00 |
| polyethylene glycol (150) distearate | 1.30 |
| Octopirox | 1.00 |
| Polymer JR | 0.20 |
| Dowicil 200 | 0.10 |
| fragrance | 0.50 |
| deionized water q.s. to | 100 |

The pH of the composition is adjusted to 7.5 by the addition of 15% HCl.

EXAMPLE 3

A detergent composition is prepared according to the process of example 1 and consists of the following ingredients:

|  | wt/wt% |
| --- | --- |
| cocoamidohydroxypropyl sultaine | 5.00 |
| TDES (4.2) | 5.00 |
| polyoxyethylene (44) sorbitan monolaurate | 12.00 |
| polyethylene glycol (150) distearate | 1.30 |

-continued

| | wt/wt% |
|---|---|
| Octopirox | 0.25 |
| Polymer JR | 0.40 |
| Dowicil 200 | 0.10 |
| fragrance | 0.30 |
| deionized water q.s. to | 100 |

The pH of the composition is adjusted to 7.2 by the addition of 15% HCl.

EXAMPLE IV-VI

The compositions of Examples I-III were evaluated for ocular irritation by the following modified Draize Test (J. H. et al., Toilet Goods Assn. No. 17, May 1952, No. 1, Proc. Sci. Sect.).

A 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial installation; second and third installations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunction with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

The results are as follows:

| Example | 1hr | 24hr | 48hr | 72hr | 96hr | Day 7 | Rating |
|---|---|---|---|---|---|---|---|
| I | 14.5 | 6.2 | 6.7 | 6.7 | 2.7 | 1.0 | Slight Irritation |
| II | 13.0 | 5.3 | 6.0 | 6.0 | 3.3 | 2.3 | Slight Irritation |
| III | 13.3 | 4.7 | 5.8 | 5.2 | 2.0 | 1.3 | Slight Irritation |

These results demonstrate that the compositions of Examples I, II and III are mild and present only a slight ocular irritation potential.

EXAMPLE VII

A shampoo composition is prepared as follows. Polymer JR is dissolved in 400 g of water with heat and stirring. The cocoamidohydroxypropyl sultaine, TDES (4.2), polyoxyethylene (44) sorbitan monolaurate (minus 25 g) and polyethylene glycol (150) distearate are added. The mixture is heated until the polyethylene glycol distearate is dissolved. The mixture is cooled and the pH is adjusted to 6.2 with 15% HCl. The Omadine MDS is added and the mixture is heated and stirred. The fragrance is mixed with the remaining 25 g of polyoxyethylene (44) sorbitan monolaurate and added to the cooled solution and the dye is then added.

The resulting composition consists of the following ingredients:

| Ingredients | wt/wt% |
|---|---|
| cocoamidohydroxypropyl sultaine | 6.88 |
| TDES (4.2) | 5.00 |
| polyoxyethylene (44) sorbitan monolaurate | 16.67 |
| polyethylene glycol (150) distearate | 1.30 |
| Omadine MDS | 0.25 |
| Polymer JR 400 | 0.40 |
| Dowicil 200 | 0.10 |
| fragrance | 0.30 |
| dye | 0.17 |
| deionized water q.s. to | 100 |

The pH is adjusted to 6.2 with 15% HCl.

EXAMPLE VIII

A shampoo composition is prepared according to the procedure of Example VII and consists of the following ingredients:

| Ingredients | wt/wt% |
|---|---|
| cocoamidohydroxypropyl sultaine | 13.26 |
| TDES (4.2) | 19.73 |
| polyoxyethylene (44) sorbitan monolaurate | 9.01 |
| polyethylene glycol (150) distearate | 1.30 |
| Omadine MDS | 0.25 |
| Polymer JR | 0.60 |
| deionized water q.s. to | 100.00 |

The pH is adjusted to 6.5 with 15% HCl. 150 g of the above shampoo was diluted to 500 g with deionized water and allowed to stand for about 10 minutes with occasional stirring. Upon dilution, the Polymer JR separates as a gel and can be removed from the solution by centrifugation. After the gel is collected, it is washed with deionized water and centrifuged twice and the gel is then analyzed by HPLC and found to contain 238 ppm Omadine MDS. This dilution simulates in use dilution of the composition and shows that the Omadine MDS is retained in the polymer-surfactant coacervate.

EXAMPLE IX

A shampoo composition is prepared according to the procedure of Example VII and consists of the following ingredients:

| Ingredients | wt/wt% |
|---|---|
| cocoamidohydroxypropyl sultaine | 13.26 |
| TDES (4.2) | 10.73 |
| polyoxyethylene (44) sorbitan monolaurate | 9.01 |
| polyethylene glycol (150) distearate | 1.30 |
| Omadine MDS | 1.00 |
| Polymer JR | 0.60 |
| deionized water q.s. to | 100.00 |

The pH is adjusted to 6.5 with 15% HCl.

When 150 g of the above shampoo are diluted to 500 g with deionized water and allowed to stand for about 10 minutes with occasional stirring upon dilution the Polymer JR separates as a gel and can be removed from the solution by centrifugation. After the gel is collected it is washed with deionized water and centrifuged twice. The gel is then analyzed by HPLC and found to contain 1136 ppm Omadine MDS. This dilution simulates in use dilution of the composition and shows that the Omadine MDS is retained in the polymer-surfactant coacervate.

EXAMPLES X and XI

The following formulations are prepared according to the procedure of Example VII and contain the following ingredients:

|  | EXAMPLE X | EXAMPLE XI |
|---|---|---|
|  | wt/wt% | wt/wt% |
| cocoamido betaine | 4.0 | 4.0 |
| amidohydroxypropyl phosphobetaine | 1.0 | 1.0 |
| TDES (4.2) | 5.0 | 5.0 |
| polyoxyethylene (80) sorbitan laurate | 3.0 | 3.0 |
| polyethylene glycol (150) distearate | 0.5 | 0.5 |
| Polymer JR | 0.4 | 0.4 |
| Dowicil 200 | 0.1 | 0.1 |
| propylene glycol | 2.3 | 2.3 |
| dyes & fragrance | 0.4 | 0.4 |
| Omadine MDS | 0.5 | — |
| Octopirox | — | 0.25 |
| deionized water q.s. to | 100 | q.s. to 100 |

The formulation of Example X is adjusted to a pH of 6.6 with dilute HCl. The composition is sparkling clear with a viscosity of about 800–900 cps.

The formulation of Example XI is adjusted to a pH of 8.0 with dilute NaOH. The product is sparkling clear.

In vivo antidandruff test studies are conducted with the above formulations as follows:

Two groups of 8 people each who have dandruff are compared using each test shampoo twice weekly over a period of three weeks. A commercial non-dandricidal shampoo is used to establish the baseline counts. The higher the corneocyte count the greater the scalp flaking and subsequent lack of dandruff control. Thus, counts are taken before and after shampoo treatment with the medicated test products. The after treatment counts are taken four days after shampooing. The results are as follows:

EXAMPLE X

| Subject | Baseline Pre-Treatment | Post Treatment |
|---|---|---|
| 1 | 994,000 | 800,000 |
| 2 | 597,000 | 326,000 |
| 3 | 602,000 | 501,000 |
| 4 | 1,098,000 | 622,000 |
| 5 | 947,000 | 776,000 |
| 6 | 543,000 | 481,000 |
| 7 | 765,000 | 655,000 |
| 8 | 901,000 | 531,000 |

EXAMPLE XI

| Subject | Baseline Pre-Treatment | Post Treatment |
|---|---|---|
| 1 | 554,000 | 510,000 |
| 2 | 672,000 | 660,000 |
| 3 | 800,000 | 619,000 |
| 4 | 541,000 | 406,000 |
| 5 | 644,000 | 389,000 |
| 6 | 580,000 | 493,000 |
| 7 | 613,000 | 501,000 |
| 8 | 606,000 | 488,000 |

The compositions of Examples X and XI each show a significant corneocyte count reduction thereby indicating excellent anti-dandruff efficacy.

EXAMPLE XII

A shampoo composition is prepared as follows:

0.2 parts by weight of Polymer JR are dissolved in 40 parts by weight of deionized water with heat and stirring, then cooled to room temperature. 16.55 parts by weight of a premelted 40% monolauryl sodium sulfosuccinate, 6.25 parts by weight of a 24% lauric-myristic imidazoline, 0.5 parts by weight of a coconut acid, 3.0 parts by weight of polyethylene glycol (150) distearate and 3.0 parts by weight of sodium sulfate are charged into a vessel equipped with a stirrer and steam and heated to 70° C., then cooled to room temperature. The mixture is slowly added to the Polymer JR solution with stirring at room temperature and 1.0 part by weight of thickener is added. The pH is adjusted to 6.5 with dilute HCl. The fragrance and dye are then added with agitation and the remaining deionized water is charged.

The resulting composition has the following formulation:

|  | wt/wt% |
|---|---|
| Omadine MDS | 0.75 |
| lauric myristic imidazoline | 1.50 |
| sodium lauryl sulfate | 4.80 |
| monolauryl sodium sulfosuccinate | 4.80 |
| Polymer JR | 0.20 |
| coconut acid | 0.50 |
| polyethylene glycol 150 distearate | 3.50 |
| Dowicil 200 | 0.10 |
| ethylene diaminetetrasodiumacetate | 0.20 |
| sodium sulfate | 3.00 |
| Acrysol ICS (Rohm & Haas tradename for an alkali-soluble acrylic polymer emulsion thickener) |  |
| dye, fragrance | 0.60 |
| deionized water q.s. to | 100.00 |

The pH is adjusted to 6.5 with dilute HCl

EXAMPLE XIII

A shampoo composition containing a sunscreen agent is prepared according to the procedure of Example XII and has the following formulation:

|  | wt/wt% |
|---|---|
| tris-octadecylphosphotriester | 0.50 |
| para-amino benzoic acid | 1.00 |
| lauric myristic imidazoline | 4.50 |
| amidohydroxypropyl phosphobetaine | 4.50 |
| amidoamine oxide | 3.00 |
| Cosmedia HSP-1180 | 0.20 |
| Dowicil 200 | 0.10 |
| fragrance | 0.60 |
| deionized water q.s. to | 100.00 |

EXAMPLE XIV

An anti-insecticide shampoo composition is prepared according to the procedure of Example XII and has the following formulation:

|  | wt/wt% |
|---|---|
| pyrethrins | 1.0 |
| piperonyl butoxide | 0.2 |
| lauric myristic imidozaline | 4.5 |
| amidohydroxypropyl phosphobetaine | 4.5 |
| amidoamine oxide | 2.0 |
| trisoctadecyl phosphotriester | 1.0 |
| Cosmedia HSP-1180 | 0.3 |

|  | wt/wt% |
|---|---|
| Dowicil 200 | 0.1 |
| fragrance | 0.6 |
| deionized water q.s. to | 100 |

EXAMPLE XV

A shampoo composition is prepared according to the procedure of Example VII and has the following formulation:

|  | wt/wt% |
|---|---|
| Octopirox | 0.75 |
| lauric myristic imidazoline | 3.00 |
| sodium lauryl sulfate | 7.50 |
| Merquat | 2.00 |
| coconut acid | 3.00 |
| Acrysol ICS | 2.00 |
| Dowicil 200 | 0.10 |
| dye, fragrance | 0.50 |
| deionized water q.s. to | 100.00 |

The pH is adjusted to 8.0 with dilute sodium hydroxide.

EXAMPLE XVI

A shampoo composition is prepared according to the procedure of Example VII and has the following formulation:

|  | wt/wt% |
|---|---|
| Omadine MDS | 1.00 |
| lauric myristic imidazoline | 3.00 |
| sodium-lauryl (3) ether sulfate | 10.00 |
| Cartaretin | 1.00 |
| hydroxypropyl methyl cellulose | 1.50 |
| Dowicil 200 | 0.10 |
| dye, fragrance | 0.25 |
| deionized water q.s. to | 100.00 |

The pH is adjusted to 6.0 with dilute HCl.

EXAMPLE XVII

An insecticidal detergent composition is prepared according to the procedure of Example XII and has the following formulation:

|  | wt/wt% |
|---|---|
| piperonyl butoxide | 0.01 |
| pyrethrins | 1.00 |
| Gafquat | 1.00 |
| lauric myristic idazoline | 3.00 |
| $C_{12}$–$C_{16}$ olefin sulfonate | 6.50 |
| alkanolamide | 0.30 |
| Acrysol ICS | 2.00 |
| dye, fragrance | 0.55 |
| deionized water q.s. to | 100.00 |

The pH is adjusted to 6.2 with HCl.

EXAMPLE XVIII

A protective shampoo composition is prepared according to the procedure of Example XVI and has the following formulation:

|  | wt/wt% |
|---|---|
| lauric myristic imidazoline | 1.50 |
| sodium lauryl sulfate | 4.80 |
| monolauryl sulfosuccinate | 4.80 |
| Polymer JR | 0.20 |
| polyvinylpyrrolidone | 1.00 |
| coconut acid | 0.50 |
| polyethylene glycol (150) distearate | 3.00 |
| sodium sulfate | 3.00 |
| dye & fragrance | 0.60 |
| deionized water q.s. to | 100.00 |

The pH is adjusted to 7.0 with HCl.

While the present invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the appended claims.

What is claimed is:

1. A detergent composition consisting essentially of
   (a) at least one anionic or amphoteric surfactant wherein the anionic surfactant is selected from the group consisting of alkyl sulfates, alkyl ether sulfates, α-olefin sulfonates, alkyl sulfosuccinates, alkyl sarcosinates, alkyl monoglyceride sulfates, alkyl monoglyceride sulfonates, alkyl benzene sulfonates, acyl isethionates and acyl methyl taurides and wherein the amphoteric surfactant is selected from the group consisting of betaines, sultaines, phosphobetaines, phosphitaines, n-alkylamino propionates, n-alkylimino dipropionates and imidazolines;
   (b) at least one water-soluble, nitrogen-containing polymer selected from the group consisting of nitrogen-containing free sulfonic acid polymers, adipic acid/dimethylaminohydroxypropyl diethylene-triamine copolymers, acrylamide copolymers, and quaternary ammonium polymers formed by the reaction product of dimethyl sulfate and a copolymer of vinyl pyrrolidone and dimethylaminoethylmethacrylate; and
   (c) at least one water-soluble non-particulate antidandruff agent selected from the group consisting of 1-hydroxy-2-pyridones and magnesium sulfate adducts of 2,2'-dithio-bis(pyridine-1-oxides).

2. The composition of claim 1 wherein the surfactant is present from about 2 to about 20% by weight of the composition.

3. The composition of claim 1 wherein the anionic surfactant is sodium lauryl sulfate.

4. The composition of claim 1 wherein the amphoteric surfactant is lauric myristic imidazoline.

5. The composition of claim 1 wherein the surfactants are sodium lauryl sulfate and lauric myristic imidazoline.

6. The composition of claim 1 wherein the water-soluble nitrogen-containing polymer is present from about 0.05 to 1.00% by weight of the total composition.

7. The composition of claim 1 wherein the water-soluble non-particulate substance is present in an amount from about 0.1 to 5.0% by weight of the total composition.

8. The composition of claim 1 containing up to about 20% by weight of the total composition of a non-ionic surfactant selected from the group consisting of the reaction product of sorbitan monolaurate with 20 to 80 moles of ethylene oxide, the reaction product of sorbitan monococoate with 20 to 80 moles of ethylene oxide, and ethoxylated fatty alcohol.

9. The composition of claim 1 containing up to about 5% by weight of the total composition of a cationic phosphotriester surfactant.

10. The composition of claim 1 wherein the water-soluble nitrogen containing polymer is an adipic acid/-dimethylaminohydroxypropyl diethylenetriamine copolymer.

11. The composition of claim 1 wherein the water-soluble, nitrogen-containing polymer is a free sulfonic acid polymer.

12. The composition of claim 1 wherein the water-soluble nitrogen containing polymer is an acrylamide copolymer.

13. The composition of claim 1 wherein the water-soluble nitrogen containing polymer is a quaternary ammonium polymer formed by the reaction product of dimethyl sulfate and a copolymer of vinyl pyrrolidone and dimethylaminoethylmethacrylate.

* * * * *